(12) United States Patent  
Wingler et al.

(10) Patent No.: US 9,149,177 B2  
(45) Date of Patent: Oct. 6, 2015

(54) MEDICAL INSERTION DEVICE

(75) Inventors: Troy W. Wingler, Martinsville, IN (US); Neal E. Bridgett, Bloomington, IN (US); Rebecca L. Walendzak, Bloomington, IN (US); Mahfuza Ahmed, Brighton, MA (US); Darryl J. Collins, Bloomington, IN (US); Shawn L. Nichols, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 209 days.

(21) Appl. No.: 13/611,316

(22) Filed: Sep. 12, 2012

(65) Prior Publication Data

US 2013/0158433 A1    Jun. 20, 2013

Related U.S. Application Data

(60) Provisional application No. 61/534,552, filed on Sep. 14, 2011.

(51) Int. Cl.
| | |
|---|---|
| *A61B 5/00* | (2006.01) |
| *A61M 25/00* | (2006.01) |
| *A61B 1/32* | (2006.01) |
| *A61M 25/09* | (2006.01) |

(52) U.S. Cl.
CPC ............ *A61B 1/32* (2013.01); *A61M 25/09041* (2013.01); *A61M 2025/09116* (2013.01)

(58) Field of Classification Search
CPC ............. A61M 25/09041; A61M 2025/09116

USPC .......................................................... 600/585  
See application file for complete search history.

(56) References Cited

U.S. PATENT DOCUMENTS

| 2004/0143219 A1* | 7/2004 | Lee et al. ................. 604/167.03 |
| 2005/0177043 A1* | 8/2005 | Windheuser et al. ......... 600/434 |
| 2007/0179472 A1* | 8/2007 | Whittaker et al. ............ 604/528 |

* cited by examiner

*Primary Examiner* — Brian Szmal  
*Assistant Examiner* — H. Q. Nguyen  
(74) *Attorney, Agent, or Firm* — Brinks Gilson & Lione

(57) ABSTRACT

A medical device is provided. The device includes a generally elongate member with distal and proximal end portions and a longitudinal axis and a lumen disposed therethrough, wherein the lumen is configured to allow the passage of a wireguide therethrough. The proximal end portion defines a trough for accepting a tip of the wireguide and urging the tip into the lumen from a varying angle of attack with respect to the longitudinal axis. The trough is defined from an open proximal end that provides communication with the lumen. The trough includes a proximal end face with an arcuate first edge that traverses only a portion of a total circumference of the elongate member. The proximal end face transitions to a second face disposed distally of the proximal end face. The second face defines a second edge that traverses another portion of the total circumference of the elongate member.

19 Claims, 7 Drawing Sheets

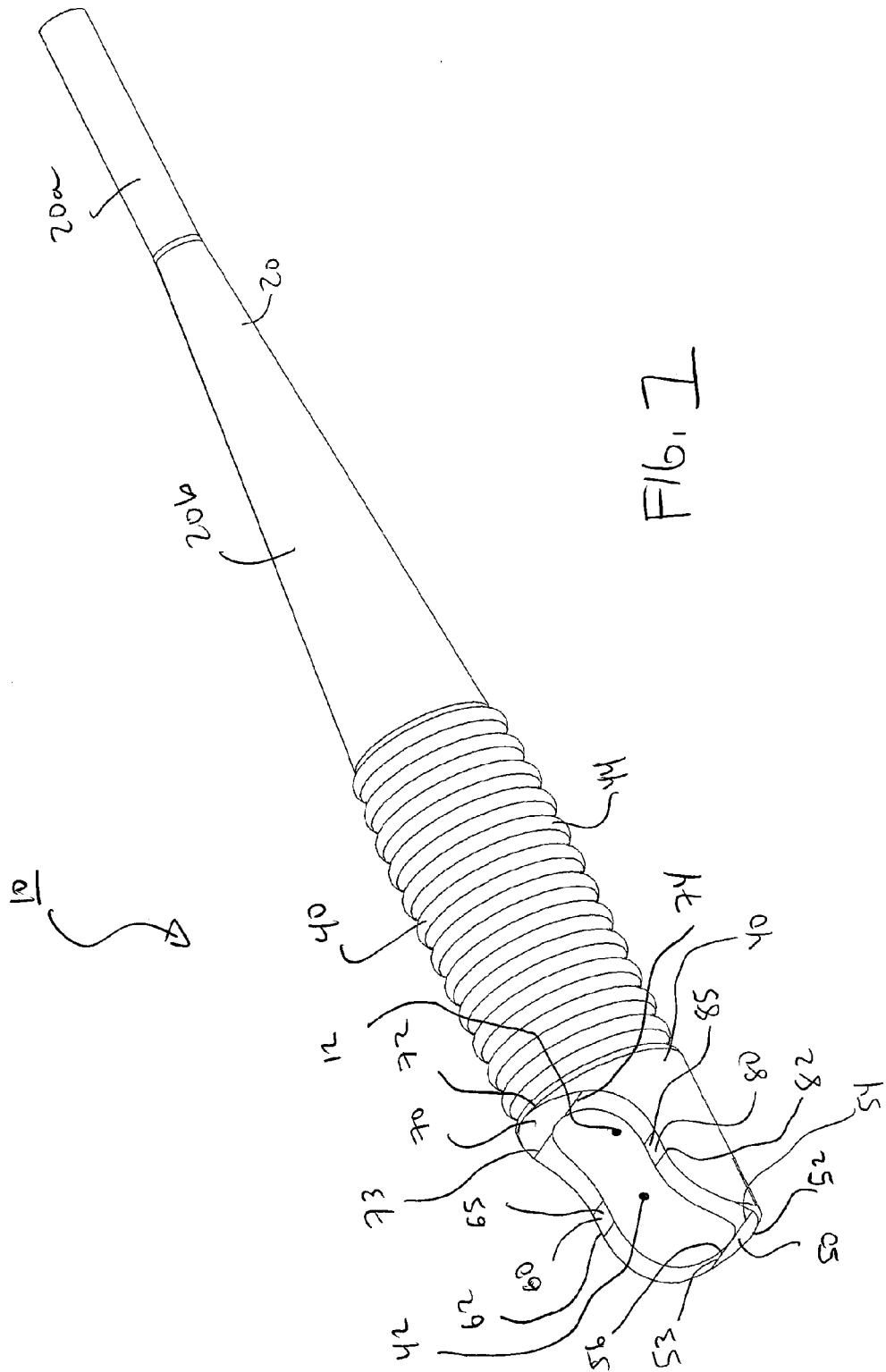

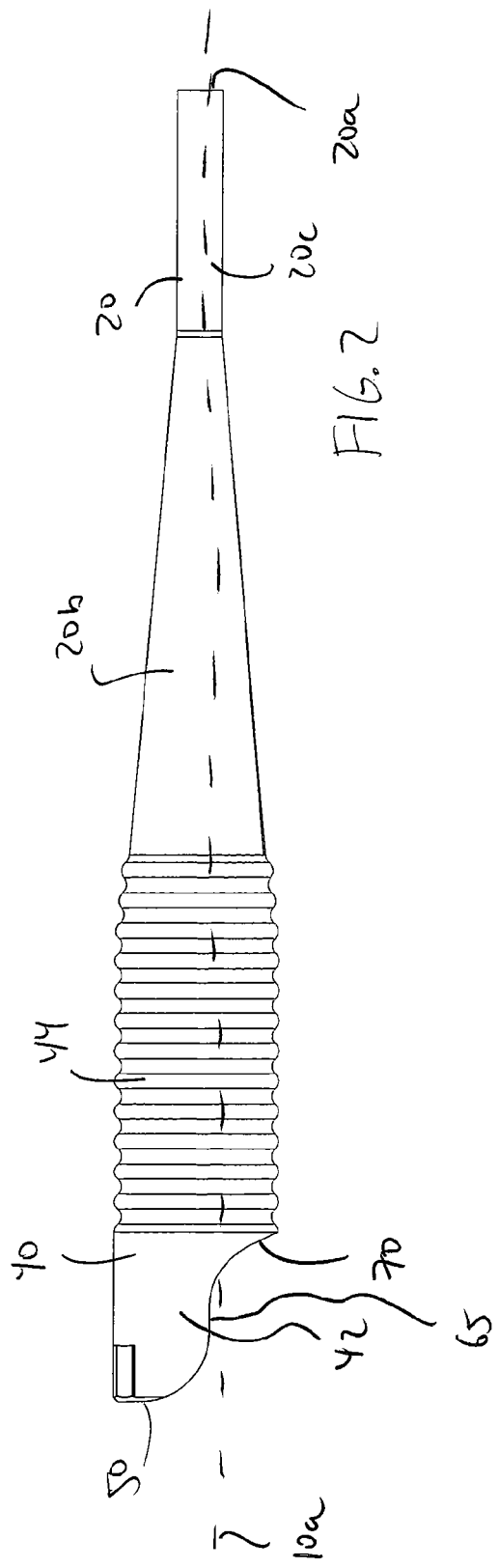

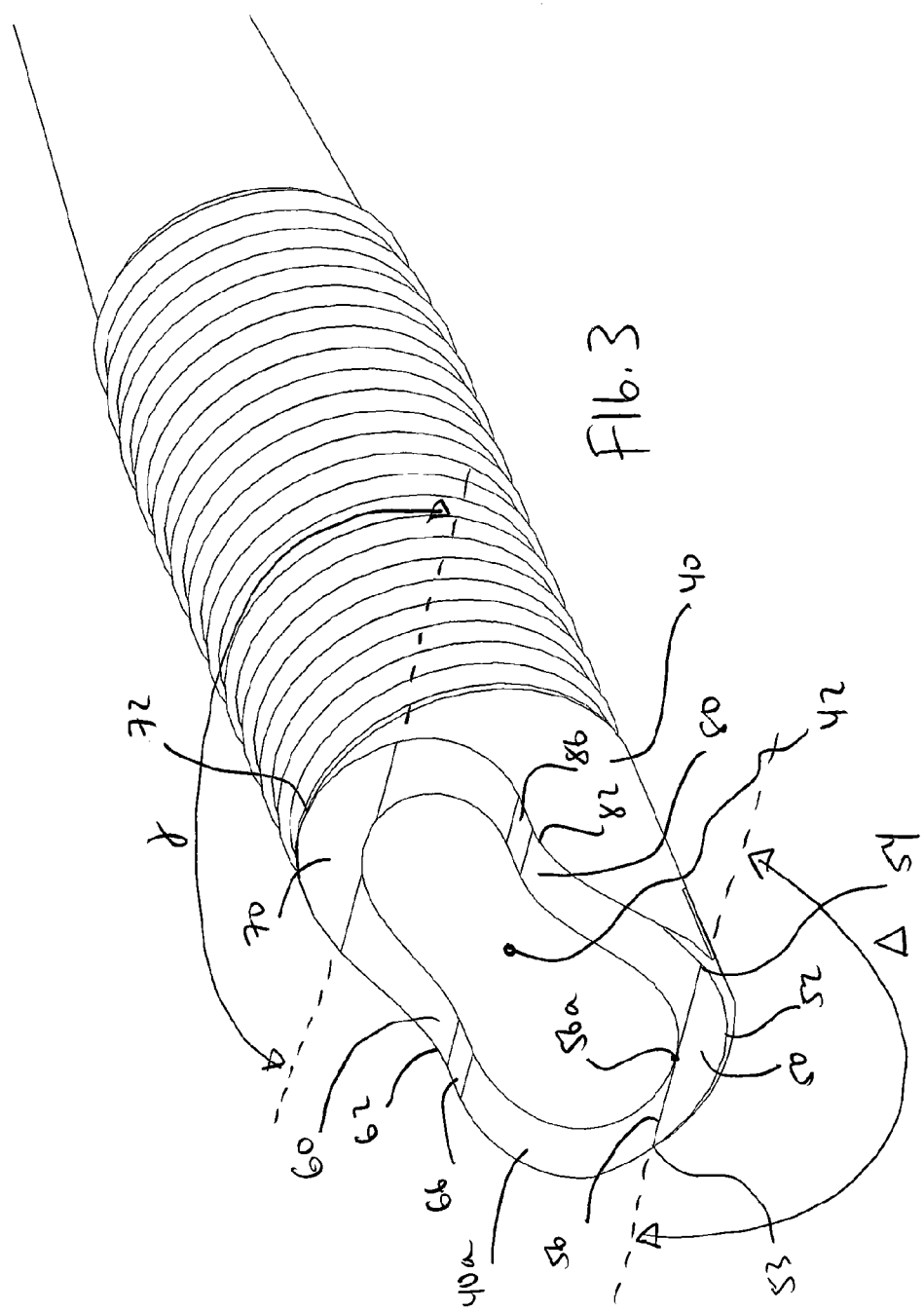

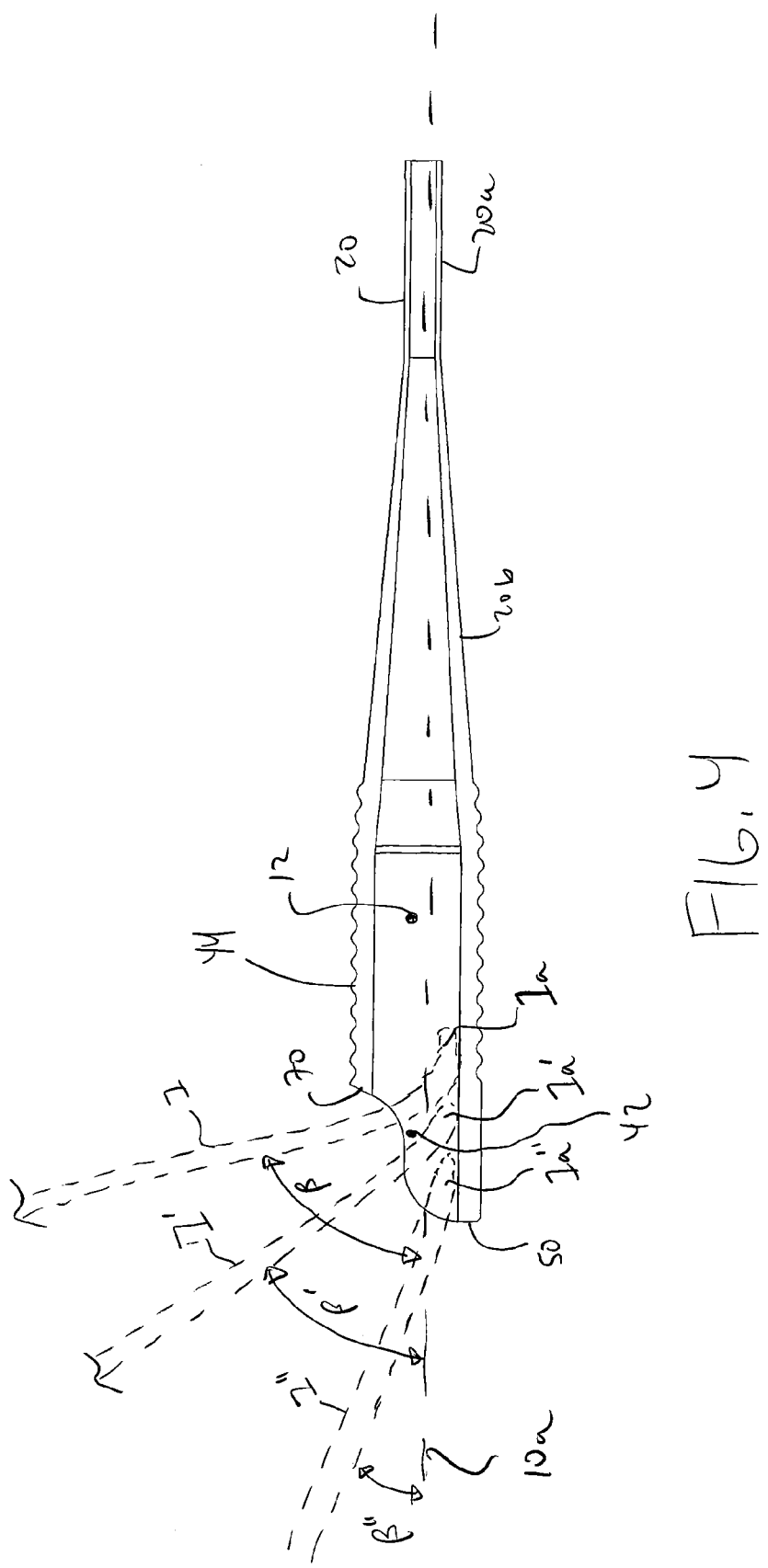

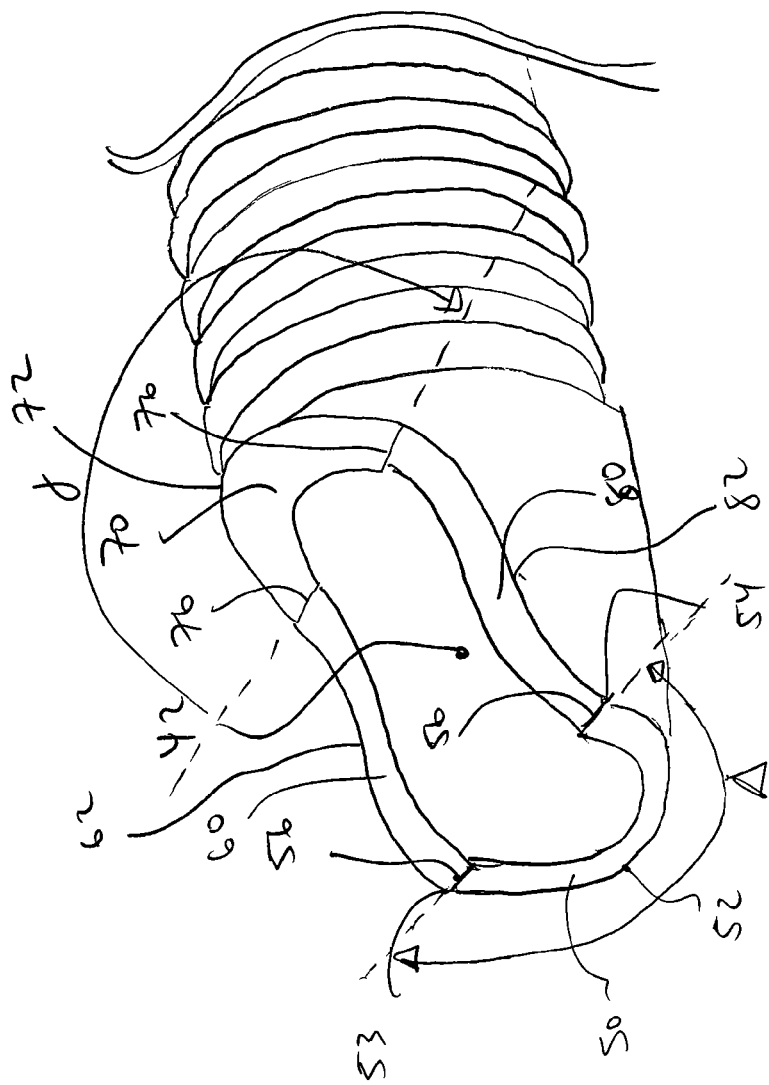

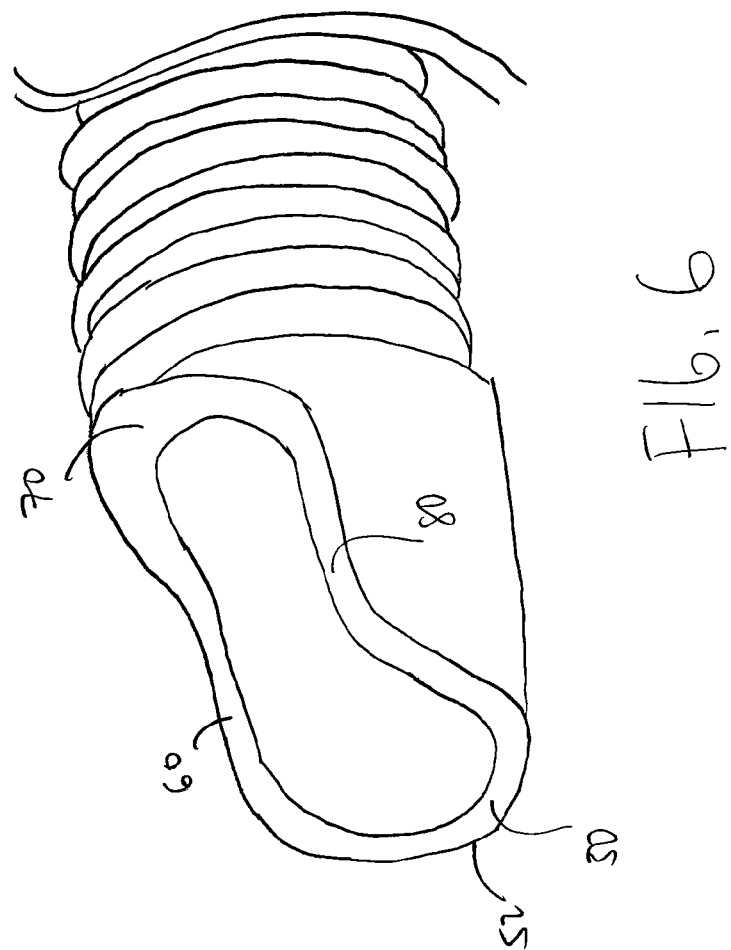

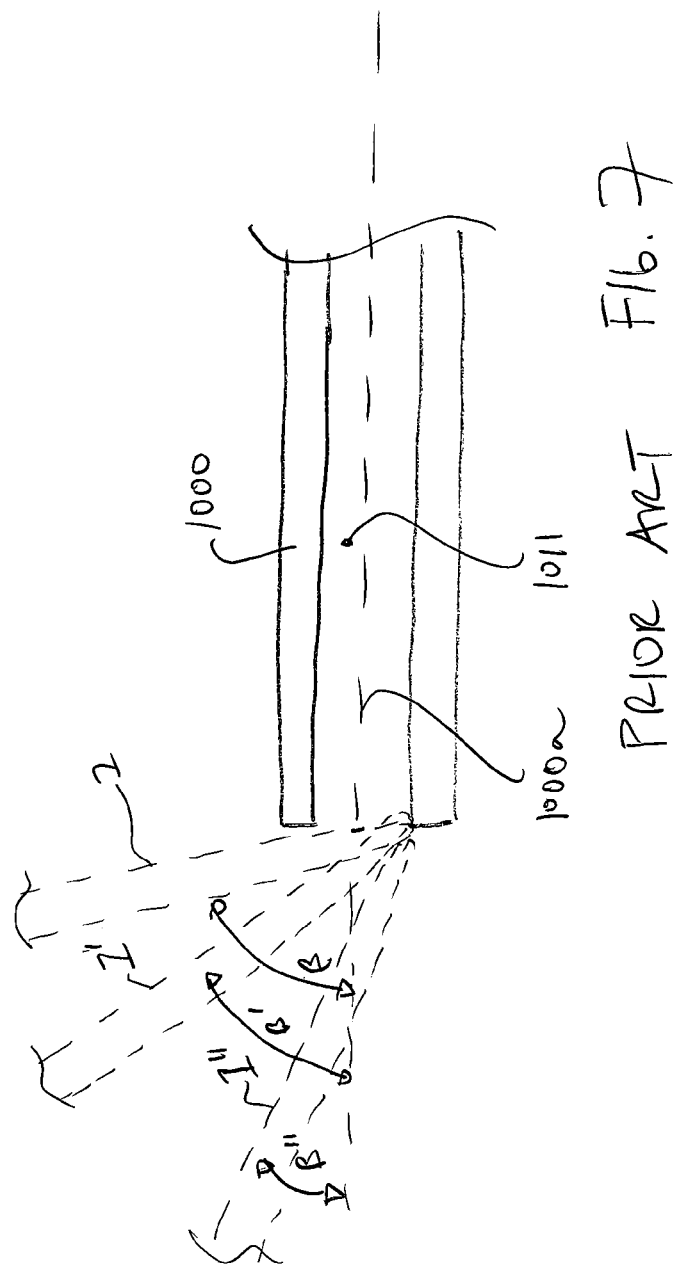

MEDICAL INSERTION DEVICE

CROSS-REFERENCE TO RELATED APPLICATIONS

This application claims priority to U.S. Provisional Application No. 61/534,552, filed on Sep. 14, 2011, the entirety of which is fully incorporated by reference herein.

TECHNICAL FIELD

This specification relates to minimally invasive medical procedures as well as procedures requiring percutaneous access to a patient. Often with medical procedures a wire guide is threaded through one or more lumens within a patient's anatomy to reach a surgical location. Another device, such as a catheter or scope may be threaded over the wire guide to allow that device to also reach the surgical field. The tips of wire guides are often necessarily floppy or relatively unstable to allow for an atraumatic use of the wire guide within the patient.

BRIEF SUMMARY

A first representative embodiment of the disclosure is provided. The embodiment includes a medical device. The medical device includes a generally elongate member with a distal end portion and a proximal end portion with a longitudinal axis and a lumen disposed therethrough. The lumen is configured to allow the passage of a wireguide therethrough. The proximal end portion of the elongate member comprises a proximal end face, the proximal end face has an arcuate first edge. The first edge circumscribes only a portion of a total circumference of the elongate member. The proximal end face transitions to a second face that is disposed distally of the proximal end face. The second face defines an arcuate second edge that circumscribes another portion of the total circumference of the elongate member.

A second representative embodiment of the disclosure is provided. The embodiment includes a medical device. The medical device includes a generally elongate member with a distal end portion and a proximal end portion with a longitudinal axis and a lumen disposed therethrough, wherein the lumen is configured to allow the passage of a wireguide therethrough. The proximal end portion defines a trough for accepting a tip of the wireguide and urging the tip into the lumen from a varying angle of attack with respect to the longitudinal axis. The trough is defined from an open proximal end providing communication with the lumen. The trough includes a proximal end face with an arcuate first edge, the first edge circumscribes only a portion of a total circumference of the elongate member. The proximal end face transitions to a second face that is disposed distally of the proximal end face, the second face defining a second edge that circumscribes another portion of the total circumference of the elongate member.

Advantages of the disclosed device will become more apparent to those skilled in the art from the following description of embodiments that have been shown and described by way of illustration. As will be realized, other and different embodiments are contemplated, and the disclosed details are capable of modification in various respects. Accordingly, the drawings and description are to be regarded as illustrative in nature and not as restrictive.

BRIEF DESCRIPTION OF THE DRAWINGS

FIG. 1 is a perspective view of a medical insertion device.
FIG. 2 is a side view of the device of FIG. 1.
FIG. 3 is a detail view of the trough of the device of FIG. 1.
FIG. 4 is a side cross-sectional view of the device of FIG. 1, schematically showing wire guides being threaded into the lumen of the device from various approach angles.
FIG. 5 is a detail view of the trough of an alternate medical insertion device.
FIG. 6 is a detail view of the trough of another alternate medical device.
FIG. 7 is a schematic drawing of attempting to thread wire guides from various angles of approach into the lumen of a conventional catheter.

DETAILED DESCRIPTION OF THE DRAWINGS AND THE PRESENTLY PREFERRED EMBODIMENTS

Turning now to FIGS. 1-4, a medical insertion device 10 is provided. The medical insertion device 10 extends between a distal end portion 20 and a proximal end portion 40. A lumen 12 is disposed through the device 10 along a longitudinal axis 10a that extends therethrough. The proximal end portion 40 includes a scooped opening 42 that is configured to receive a distal end 1a of a wire guide 1 (FIG. 4) and urge the distal end 1a of the wire guide 1 to be threaded through the lumen 12 and ultimately out of the device 10 through an aperture 21 defined at an end surface of the distal end portion 20.

The distal portion 20 may include a distal tip 20a that is configured to mate with and/or extend within a lumen of a working device, such as a catheter, scope, or the like that is to be passed into a patient to assist with a medical procedure. In some embodiments, the distal end portion 20 may include a conical section 20b with a decreasing diameter toward the distal end thereof, with an end of the conical section 20b forming the distal end. Alternatively, the distal portion 20 may additionally include a cannula portion 20c with a substantially constant outer diameter to extend further within the lumen of the working device, or for another purpose, such as puncture device for a valve or an adapter. The relatively small outer diameter at the distal tip 20a of the device provides for extending the distal tip 20a within the working device, and also projecting the wire guide from the distal tip 20a in a specific direction.

In some embodiments, the proximal portion 40 may include a plurality of ridges 44 disposed upon the outer surface thereof, which are ergonomically disposed to allow the user to easily grip and manipulate the insertion device 10. The ridges 44 may be at a constant diameter (and ridge height) or they may vary along the length of the proximal portion 40. In some embodiments, the ridges 44 extend from just distally of the inner end face 70 (discussed below, which defines an opening into the trough 42), while in other embodiments, the ridges 44 may be disposed in other portions of the device 10.

As shown in FIG. 4, the lumen 12 along the device 10 may be formed with the same general profile as the outer surface of the device 10, such that the wall thickness of the device 10 is substantially constant along the length of the device 10 (not including the built up wall thickness forming the plurality of ridges 44). In some embodiments, a distal portion of the lumen 12 may be formed with a smaller inner diameter than an inner diameter of a portion of the lumen proximate the inner end face 70, to allow the overall distal end portion 20 of the device 10 to include the conical section 20b, which may have a decreasing inner diameter at a constant rate, or a differing rate. In some embodiments, the transition between the constant diameter portion of the lumen (which partially or entirely falls within the ridged portion 44) may additionally be within the ridged portion of the device 10 such that the conical section 20b of the device 10 additionally includes one or more of the plurality of ridges 44.

As shown schematically in FIG. 4, the scooped opening 42 is configured to receive the distal end 1a of the wire guide 1 and urge the wire guide 1 to be threaded through the lumen 12 when the distal end 1a approaches the lumen 12 at a large range acute angles of attack β with respect to the longitudinal axis 10a of the device 10, as shown schematically in FIG. 6. Moreover, the presence of the scooped opening 42 allows the distal end 1a of the wire guide 1 to approach the device 10, not just at a proximal end surface as required when a wire guide is to be threaded directly in the lumen of a catheter, scope, or the like (shown schematically in FIG. 7 depicting this conventional process), but rather the wire guide 1 may approach the scooped opening 42 at any position along its length, between the proximal end face 50 and the second end face 70 (as discussed in further detail below). Wire guides 1, 1', and 1" are drawn schematically with various relatively steep angles of attack β (β', β") and approaching the scooped portion 42 distally of the proximal end face 50, while still ultimately causing the distal tip 1a (1a', 1a") of the wire guide to be threaded within the lumen 12 and ultimately through the device 10 and into the lumen of the working device (such as a catheter, scope, or the like). As shown schematically in FIG. 7, these angles of attack β, β', β" and relative positions of the wire guide 1 (1', 1") with respect to the opening into the lumen 1011 of the working device 1000 may not result in a successful thread by the medical professional, or at least requires significantly more precision by the medical professional at locating the distal tip of the wire guide with respect to the opening into the lumen 1011.

As can be understood with thorough review and understanding of this disclosure, the relatively large range of potential angles of attack β provides for improved efficiency in threading a wire guide 1 through the device 10 and ultimately through a catheter, scope, or other elongate member with a relatively small working lumen. This range of angles of attack β is significantly larger than the range of potential angles of attack when inserting a distal end 1a of a wire guide 1 directly into the lumen 1011 of the catheter, scope, and the like (depicted schematically as 1000 in FIG. 7).

The proximal end portion 40 of the device 10 includes a proximal end face 50 that defines the proximal-most edge of the device 10. The proximal end face 50 may be disposed substantially perpendicular to the longitudinal axis 10a of the device 10, or alternatively, may extend at an acute angle to the longitudinal axis 10a, or at other orientations (such as in an arcuate relationship, a non-planar and non-curved orientation, e.g. waved or discontinuous fashion) or in other shapes and orientations.

As best shown in FIG. 3, the proximal end face 50 may include an outer edge, or first edge, 52 that establishes the edge between the proximal end face 50 and the outer circumferential surface 40a of the proximal end portion 40 of the device. The proximal end face 50 is provide with an arc length Δ (along its outer edge 52) that traverses a portion of, but not the entirety of the total outer circumference of the proximal end portion 40 of the device 10. In some embodiments, the arc length Δ of the outer edge 52 may be within the range of about 30 degrees to about 210 degrees, inclusive of all arc lengths therewithin, or within the range of about 90 degrees to about 180 degrees, inclusive of all arc lengths therewithin, or within the range of about 90 degrees to about 150 degrees, inclusive of all arc lengths therewithin. In some preferred embodiments, the arc length Δ of the outer edge 52 may be between 80 to about 110 degrees, inclusive of all arc lengths therewithin. One or ordinary skill will understand after a thorough review of this disclosure that the performance of the device 10 may be optimized with various arc lengths Δ and distances between the proximal end face 50 and the inner end face 70 (discussed below) to maximize the potential angles and locations of attack of a wire guide 1 to the trough 42 (and ultimately thread the wire guide 1 through the lumen 12 of the device), while providing a device with sufficient strength to prevent inadvertent breakage during manufacture, storage, and use.

The proximal end face 50 may be additionally bounded by an enclosing edge, or curve 56 that defines another boundary of the proximal end face 50. In some embodiments as best shown in FIG. 3, the enclosing edge 56 meets with opposite ends 53, 54 of the outer edge 52, such that the combination of the outer edge 52 and the enclosing edge 56 defines the entire periphery of the proximal end face 50. In other embodiments, additional edges may assist with the outer edge 52 and the enclosing edge to fully define the periphery of the proximal end face 50. In some embodiments shown in FIG. 3, the enclosing edge 56 forms a straight line and engages opposite end 53, 54 of the outer edge 52. In this embodiment, the enclosing edge 56 is a straight line, with a center point 56a that forms an edge with the proximal-most opening into the internal volume 42a of the trough 42. In other words, the enclosing edge 56 forms the longest continuous chord possible. As will be appreciated, the material thickness of the device 10 and the arc length of the outer edge 52 may define or constrain the size, shape, and orientation of the enclosing edge 56. In other embodiments shown in FIG. 3a, the outer edge 52 may have a longer arc length Δ than depicted in FIG. 5, which would necessitate a similar enclosing edge to include two discrete segments positioned on opposite sides of the internal volume of the trough 42 (or the lumen 12 as it extends through the trough 42).

The trough 42 is further defined from an inner end face 70 that may be provided upon a substantially opposite circumferential side form the proximal end face 50. The inner end face 70 may be disposed distally of the proximal end face 50, and is defined, in part from an arcuate second edge 72, which establishes the edge between the inner end face 70 and another portion of the outer circumferential surface 40a of the proximal end portion 40. In a preferred embodiment, the second edge 72 traverses a second arc length γ that traverses for a portion of, but not the entirety of the total outer circumference of the proximal end portion 40. In some embodiments, the combination of the arc length Δ and second arc length γ is a portion of the outer circumference less than the total outer circumference of the proximal end portion 40. In some embodiments, the second arc length γ of the second edge 72 may be within the range of about 30 degrees to about 210 degrees, inclusive of all arc lengths therewithin, or within the range of about 90 degrees to about 180 degrees, inclusive of all arc lengths therewithin, or within the range of about 90 degrees to about 150 degrees, inclusive of all arc lengths therewithin. In some preferred embodiments, the second arc length γ of the second edge 72 may be between 80 to about 110 degrees, inclusive of all arc lengths therewithin. As with the arc length Δ, one of ordinary skill in the art will understand, upon review of the subject specification, that the second arc length γ may be optimized using some or all of the design factors discussed above.

As shown in FIG. 5, the combined arc length of the outer edge 52 and the second edge 72 may almost, or completely traverse the outer circumference of the proximal end portion 40. In embodiments where the outer edge 52 and the second edge 72 completely traverse the outer circumference of the proximal end portion, the combined outer and second edges may transition continuously with each other as shown in FIG. 6, while in other embodiments (FIGS. 3, 5) the outer and second edges 52, 72 may transition discontinuously with each other, such that the outer and second edges 52, 72 are each bounded by discrete enclosing edges 56, 76, respectively. In embodiments where the outer edge 52 and the second edge 72 transition continuously (with the transition portions 60, 80 (discussed below) therebetween, there are no enclosing edges formed, rather the edges transition with continuous curves. These embodiments minimize or eliminate the arc lengths of the first and second transition portions 60, 80, discussed below. As can be appreciated with reference to FIG. 3, the first and second transition portions 60, 80 may include a portion thereof 66, 86 that is substantially parallel to the longitudinal axis or one or both of the first and second transition portions 60, 80 may be substantially entirely or entirely parallel to the longitudinal axis along their length.

In some embodiments the proximal end face 50 may oriented substantially perpendicularly to the longitudinal axis 10a of the device 10. This orientation limits the overall length of the device 10 while maintaining the desired dimensions of the trough. In other embodiments, the proximal end face 50 may be disposed at an acute angle with respect to the longitudinal axis, which minimizes the transition angle between the proximal end face 50 and each of the first and transition portions 60, 60. The inner end face 70 may be disposed at a perpendicular angle or an acute angle with respect to the longitudinal axis 10a of the device 10.

As best shown in FIG. 3, the trough 42 may be further defined by first and second transition portions 60, 80. The first transition portion 60 extends between the proximal end face 50 and the inner end face 70 and includes an outer edge 62 that extends between the outer edge 52 and the second edge. The second transition portion 80 extends between opposite ends of the proximal end face 50 and the inner end face 70, and includes an outer edge 82 that extends between the outer edge 52 and the second edge 72. In some embodiments, the transition between the one or both of the first and second transition portions and the neighboring proximal end face 50 and the inner end face 70 is continuous (FIG. 6), while in other embodiments, the enclosing edges 56, 76 are formed between one or both of the first and second transition portions 60 and the proximal end face 50 and the inner end face 70 (FIG. 5). In some embodiments, the entire, or a portion, of one or both of the first and second transition portions 60, 80 extend substantially perpendicularly to the longitudinal axis 10a of the device 10.

While the preferred embodiments of the disclosure have been described, it should be understood that the disclosure is not so limited and modifications may be made without departing from the invention. The scope of the invention is defined by the appended claims, and all devices that come within the meaning of the claims, either literally or by equivalence, are intended to be embraced therein.

The invention claimed is:

1. A medical device comprising:
an elongate member with a distal end portion and a proximal end portion with a longitudinal axis and a lumen disposed therethrough, wherein the lumen is configured to allow the passage of a wireguide therethrough;
the proximal end portion of the elongate member comprises a proximal end face, the proximal end face has a first edge, the first edge traverses only a portion of a total circumference of the elongate member, the proximal end face transitions to a second face that is disposed distally of the proximal end face, the second face defining a second edge that traverses another portion of the total circumference of the elongate member, wherein each of the first edge and the second edge define at least a portion of a trough that allows for communication into the lumen from the proximal end portion, wherein a cross-section of the trough when viewed in a direction coaxial with a longitudinal axis of the device includes a first cross-sectional area, and a second cross-section of the trough when viewed from a perpendicular angle with respect to the longitudinal axis includes a second cross-sectional area that is greater than zero.

2. The medical device of claim 1, wherein the first edge transitions continuously with the second edge.

3. The medical device of claim 1 wherein the proximal end face transitions continuously with the second face.

4. The medical device of claim 1, where the combined first edge and the second edge traverse less than the total circumference of the elongate member.

5. The medical device of claim 4, further comprising a planar first transition face defining a first transition edge that traverses a portion of the total circumference of the elongate member and is disposed between a first end of the first edge and a first end of the second edge.

6. The medical device of claim 4, wherein a portion of the first transition face edge is parallel to the longitudinal axis.

7. The medical device of claim 5, wherein the proximal end face is perpendicular to the longitudinal axis and the second face is disposed at an acute angle with respect to the longitudinal axis.

8. The medical device of claim 5, further comprising a second transition face defining a second transition edge that traverses a remaining portion of the total circumference of the elongate member and is disposed between a second end of the first edge opposite from the first end and a second end of the second edge opposite the first end, wherein the combined first edge, second edge, first transition edge, and second transition edge traverse the total circumference of the elongate member.

9. The medical device of claim 8, wherein the first edge, the first transition edge, the second edge, and the second transition edge extend between each other in a continuous manner.

10. The medical device of claim 8, wherein the proximal end face, the first transition face, the second face, and the second transition face establish a continuous end surface of the proximal end portion of the elongate member.

11. The medical device of claim 1, wherein a radius of the first edge is the same as a radius of the second edge.

12. The medical device of claim 1, wherein an outer surface of the elongate member comprises a plurality of ridges disposed distally from the second edge.

13. The medical device of claim 1, wherein the lumen comprises an annulus with a smaller inner diameter than an inner diameter of a portion of the lumen proximate the second edge.

14. The medical device of claim 1, wherein the lumen comprises a proximal portion at a constant first diameter, and a distal portion with an continuously decreasing inner diameter.

15. The medical device of claim 12, wherein the lumen comprises a proximal portion at a constant first diameter, and a distal portion with an continuously decreasing inner diameter, wherein a discontinuity between the proximal and distal portions of the lumen is disposed within a section of the elongate member defining the plurality of ridges.

16. A medical device comprising:
an elongate member with a distal end portion and a proximal end portion with a longitudinal axis and a lumen disposed therethrough, wherein the lumen is configured to allow the passage of a wireguide therethrough;

wherein the proximal end portion defines a trough for accepting a tip of the wireguide and urging the tip into the lumen from a varying angle of attack with respect to the longitudinal axis, the trough is defined from an open proximal end providing communication with the lumen including a proximal end face with a first edge, the first edge traverses only a portion of a total circumference of the elongate member, the proximal end face transitions to a second face that is disposed distally of the proximal end face, the second face defining a second edge that traverses another portion of the total circumference of the elongate member, wherein the trough is partially defined from each of the first and second edges.

17. The medical device of claim 16, further comprising a first transition face disposed between respective first ends of the proximal end face and the second face, and a second transition face disposed between respective second ends opposite from the respective first ends of the proximal end face and the second face.

18. The medical device of claim 17, wherein the first and second transition faces define first and second transition edges, respectively, wherein the first edge, the first transition edge, the second edge, and the second transition edge extend between each other in a continuous manner.

19. The medical device of claim 16, wherein the first edge extends between an arc length within a range of between 30 degrees and 90 degrees and the second edge extends about an arc length within a range of between 30 degrees and 90 degrees.

\* \* \* \* \*